(12) United States Patent
Ross et al.

(10) Patent No.: US 6,607,368 B1
(45) Date of Patent: Aug. 19, 2003

(54) LINEAR PUMP AND METHOD

(76) Inventors: Anthony Ross, 3546 Maybank Hwy., John's Island, SC (US) 29455; Peter A. Guagliano, 2285 Marsh Hen Dr., John's Island, SC (US) 29455

( * ) Notice: Subject to any disclaimer, the term of this patent is extended or adjusted under 35 U.S.C. 154(b) by 33 days.

(21) Appl. No.: 10/008,314

(22) Filed: Nov. 3, 2001

(51) Int. Cl.[7] .......................... F04B 43/00; F04B 43/08; A61M 1/00
(52) U.S. Cl. .................. 417/412; 417/478; 604/153
(58) Field of Search .................................. 417/412, 478, 417/392, 394; 604/153; 210/321.78, 323.2

(56) References Cited

U.S. PATENT DOCUMENTS

| | | | |
|---|---|---|---|
| 1,546,973 A | * 7/1925 | Ellis | 417/472 |
| 4,076,467 A | * 2/1978 | Persson | 417/478 |
| 5,676,162 A | 10/1997 | Larson, Jr. et al. | 128/899 |
| 5,676,651 A | 10/1997 | Larson, Jr. et al. | 604/33 |
| 5,693,091 A | 12/1997 | Larson, Jr. et al. | 623/3.27 |
| 5,722,930 A | 3/1998 | Larson, Jr. et al. | 600/16 |
| 5,758,666 A | 6/1998 | Larson, Jr. et al. | 417/418 |
| 5,879,375 A | 3/1999 | Larson, Jr. et al. | 607/30 |
| 5,964,580 A | * 10/1999 | Taga | 417/394 |
| 6,352,455 B1 | * 3/2002 | Guagliano et al. | 440/38 |
| 6,464,476 B2 | * 10/2002 | Ross et al. | 417/478 |

* cited by examiner

Primary Examiner—Charles G. Freay
Assistant Examiner—Michael K. Gray
(74) Attorney, Agent, or Firm—Loren G. Helmreich; Browning Bushman P.C.

(57) ABSTRACT

A linear pump for pumping a fluid includes a generally tubular shaped bladder 50 sealingly engaged on each end to an end cap 20, 25, forming an inner chamber 14, and including each of an inlet 70 and an outlet 75 inner chamber check valve to fluidly interconnect the inner chamber with the fluid. Each of a plurality of linear motors 40 each may be connected on one end to a respective support rib 30 and on an opposing end pivotally connected to one of the end caps. The support ribs are flexible and have a central portion of the rib engaged with a central portion of the bladder. The plurality of linear motors may be selectively actuated to cause the plurality of support ribs to alternately flex and/or straighten out such that the bladder is condensed or expanded respectively to effect a change in volume of the inner chamber, thereby drawing in or displacing fluid. Bladder extensions 160 may be used to slidably connect the bladder to a respective rib.

22 Claims, 4 Drawing Sheets

LINEAR PUMP AND METHOD

FIELD OF THE INVENTION

The present invention relates to a linear pump having a flexible, generally tubular bladder. The linear pump of the present invention is relatively simple and thus inexpensive to manufacture and maintain, yet has a surprisingly high pump efficiency. The pump may be used to pump a variety of fluids and may be used in various industrial, commercial, medical, astronautical, aeronautical, or military applications.

BACKGROUND OF THE INVENTION

Pumps have been used for centuries and various types of pumps have been devised, including positive displacement pumps, rotary pumps, vane pumps, centrifugal pumps, and the Archimedes screw pump. While many of these pumps are well suited for particular uses, pumps in general do not have a high efficiency and may not be well suited for special applications, such as pumping blood or pumping sewage wastewater. Many pumps cause damage to the blood components as these blood components make either direct contact or near contact with the surfaces of the pump. Such pumps may also tend to "shear" the non-neutonize blood fluid, which may further damage blood components. Ventricular assist pumps currently employ mechanisms to move blood that stresses the blood in some situations and are non-pulsatile.

When pumping blood, constant flow by conventional pumps may cause "pump-head" because of the sustained vasodilation which results in decreased oxygen and nutrients in the area close to the vascular wall. The alterations in the cellular components of the blood, typical with rotary and constant flow pumps, may be due to reactions with the vasodialated capillaries and the components of the blood reacting to this abnormal state. Ischemia may be present due to the decreased lumen secondary to an accumulation of platelets and/or the blood not pulsing enough to create turbulence and transfer the gases and nutrients. Memory loss and neurological deficits also may be due to the hemodynamics of fluid flow of blood, a non-Newtonian fluid under sustained pressure. The pulse flow preferably allows for a psychological pause in the short duration dilated phase and the contraction which contributes to the turbulence necessary to facilitate the movement of the blood components.

Various types of linear pumps have been devised, including linear pumps particularly intended for pumping blood. U.S. Pat. Nos. 5,676,162 and 5,879,375 disclose reciprocating pump and linear motor arrangements for pumping blood. The assembly includes a piston-valve that is placed at the inlet end of a hollow chamber. The valve leaflets may be in any arbitrary position. The pump module arrangement may occupy a space of no more than approximately 6 cm. in diameter and 7.5 cm. long. In a preferred embodiment, a quick connect locking system may be utilized, as shown in FIG. 3 of the '162 Patent. FIG. 11 of the '375 Patent illustrates the anatomical arrangement of a surgically implantable pump, with a reciprocating piston-valve. Other patents directed to implantable pumps and or linear pumps include U.S. Pat. Nos. 5,676,651, 5,693,091, 5,722,930, and 5,758,666.

Conventional pumps have long been used to pump a slurry consisting of a fluid and a solid or semi-solid material, as is common in sewage wastewater. Conventional wastewater pumps have significant problems due to pump plugging and abrasion, which increases repair and maintenance costs, and results in poor pump efficiency and/or short pump life.

U.S. patent application Ser. No. 09/747,832, filed Dec. 22, 2000, by Dr. Anthony Ross and Dr. Peter Guagliano, discloses a linear pump and method, including a housing enclosing a bladder engaged on each end to an end plate, thereby forming two chambers within the housing, one of which is within the bladder. Each end plate provides at least one inlet port and outlet port, which may also include check valves therein to control the direction of fluid flow through the pump housing. The pump may operate in a positive displacement manner by reciprocating one end plate toward and then away from the opposing end plate, thereby altering chamber volumes to cause a pumping action of the fluid. However, end plate movement within the housing may cause component friction and wear surfaces between the moving end plate and the housing. In addition, in some embodiments, inertial energy losses from moving the end plate may impede pump efficiency. The moving end plate may also contribute to pump noise and/or caviation, both of which may be key factors for silent propulsions systems, such as with submarines. In still other embodiments, problems may be experienced as the moving end plate reciprocates in an axial direction that is against the direction of fluid flow, such as when the moving end plate moves toward the opposing end plate, thereby potentially creating downstream back-flow or pressure reduction problems which may significantly reduce pump efficiency.

The disadvantages of the prior art are either overcome or are reduced by the present invention, and improved linear pumps and methods of pumping fluids are hereinafter disclosed which overcome many of the disadvantages of prior art pumps, including relatively high cost of manufacture and/or poor pump efficiency.

SUMMARY OF THE INVENTION

The present invention is directed to a versatile, reliable, and relatively low-maintenance linear pump. In one embodiment, the pump may be used for pumping blood through a living body and may include a pump housing having an inlet end cap and an outlet end cap in sealed engagement with the housing. A conforming bladder may be positioned within the housing, also secured to each end cap, thereby forming two chambers within the housing. An inner chamber may be formed within the bladder, while an outer chamber may be formed by the annular area external to the bladder and internal to the housing. Each chamber may be fluidly connected with at least one inlet port and at least one outlet port, with each port containing a check-valve to control fluid flow through the pump.

Each end plate may be axially fixed with respect to the position of the opposing end plate. The pump may include a plurality of ribs extending generally parallel with a central axis through the pump housing and circumferentially spaced interior or exterior of the bladder. Each rib is attached along a portion of its length to the bladder, and may be integral between bladder layers. Each rib may be engaged with a linear motor to cause the rib to extend or retract with respect to the linear motor. The ribs may be formed to flex or bow when moved with respect to the linear motor, such that the plurality of ribs may in concert act to apply lateral forces upon the bladder, thereby distorting the shape of the bladder with respect to a bladder resting shape. Depending upon the direction of flexion, such distortion may cause a constriction or an expansion of the bladder such that the volume of the inner bladder changes inversely with the volume of the outer chamber. To control the direction of flexion, the ribs may preferably be formed relatively slat-like, or oval shaped, such that a natural direction of flex or bending is achieved. A plurality of bladder extensions may each include an enlarged end for sliding within a slot in a respective rib.

After distorting the bladder in a first direction, the linear motor force may be relaxed or reversed to cause the ribs to allow the bladder to return to the resting shape, or to force the bladder into a second distorted shape. Such action may be cyclically repeated by the linear motor, ribs and bladder, thereby effecting a pumping action of fluid through the pump housing, at a desired pump or pulse rate. A power supply and a pump controller may be provided for controlling movement of the linear motors and movement of the ribs, thereby controlling the pump rate, volume, and pressure.

The pump may be used extra-corporeal as a single unit to move blood through the inner chamber and a lubricant/thermal fluid through the outer chamber to maintain a comfortable state for the patient treated. Another embodiment may utilize the inner chamber for fluid movement to realize the benefit of a parastalyic movement.

In other embodiments, the bladder may be a selective or semi-permeable membrane, such that a selected portion of fluid may pass from one chamber to the other, while the remaining fluid and material is pumped from the first chamber. Such capability may be useful in a dialysis-like setting or in a larger embodiment for removing a portion of the fluid phase from sewage slurry.

In still another embodiment, the pump may be used intra-corporeal or extra-corporeal to assist the heart as a ventricular assist device with configuration and attachment such as is found in the Heart Mate II LVAS.

In yet another embodiment, the pump can be used as a wastewater or sewage pump to cyclically move the ribs and bladder to vary the volume of both the inner chamber and the outer chamber, thereby creating hydraulic propulsion and mixing forces through one or more discharge ports and pumping the wastewater or sewage slurry.

The pump according to the present invention may use linear motors that utilize magnetic explusion and/or contraction forces to move the ribs. Because the end plates are fixed with respect to each other, the ribs are thereby caused to bow in response to the forces imposed by the linear motor. The ribs may be formed to bow or flex in a selected direction, preferably radially with respect to the bladder central axis, thereby acting upon the bladder to create a positive-displacement volume change within the bladder. Such displacement results in pumping forces from within the bladder.

In a preferred embodiment, the flexible bladder may be formed to maintain an hour-glass shape when in a resting state, free from by external forces. Conversely, the ribs may be formed to be substantially straight and parallel to the bladder axis, when in a resting state. When the ribs are secured to the bladder, such as through lengthwise pockets within the bladder wall, the bladder and ribs together may conform to a neutral resting state. In one embodiment, elastic deformation of the bladder by drawing the ribs into the linear motor stator can store elastic potential energy in the bladder to assist with reciprocating the bladder during pumping. Thereby, the linear motors may be single-acting in one direction, such as causing the bladder to expand and increase the volume of the inner chamber. For example, the linear motors may be momentarily activated, drawing the ribs into the motors to enlarge the inner chamber in the bladder back to an expanded state. Thereafter, the motors may be deactivated and the stored elastic potential energy in the bladder may assist in discharging fluid contents from the inner chamber as the bladder returns to the neutral or resting state.

In another embodiment, the linear motors may be double-acting such that they may be reversed or activated during each phase of the pumping cycle. The double-acting motor can act in one direction to draw the ribs into the motors, thereby expanding the bladder and inner chamber volume, and then reverse to act in an opposing direction to cause the ribs to flex or bend, condensing or collapsing the bladder radially inward, effecting discharge of fluid contents from within the bladder. To pump fluid, the pump may utilize both an inner chamber, internal to the bladder, and a corresponding outer chamber operating cooperatively with the inner chamber to pump fluid from an outer, annular chamber between an inner surface of the housing and an outer surface of the bladder. The outer chamber may fill with fluid while the inner chamber is discharging fluid, and conversely, the inner chamber may fill while the outer chamber is discharging.

In one embodiment, the pump is used as a blood pump and two bladders are provided, preferably with counter offset check valves to ideally balance the pump operation with due concern to output demands. For this embodiment, the chamber exterior of the bladders may be vented to ambient, or alternatively may be provided with another desired fluid.

It is a feature of the invention that the pump may utilize valves which include polymer reeds that are in a tricuspid and/or bicuspid configuration similar to that of a human heart valve. Each valve in the device may be sized analogous to cardiac portions in the heart valve. The valves preferably are self-cleaning and quiet, and also have high efficiency and longevity.

Another feature of the invention is the use of bladder extensions to slide within a slot of a respective rib.

It is a further feature of the invention that the material which provides the helix reinforcement may be formed of a carbon fiber, an aromatic polyamide fiber, such as Kevlar, or currently advanced reinforcement which has significantly better fatigue properties than metal wire.

It is another feature of the invention that when the pump is used as a wastewater pump, the bladder may be permeable such that relatively dirty wastewater may pass from the interior of the bladder through the bladder and to the exterior of the bladder, thereby minimizing the volume of relatively dirty wastewater which must be treated.

A related feature of the invention is that the pump may be useful for pumping fluid-solid slurries containing a high percentage of solids and/or abrasives in that relatively few moving parts may be exposed to the pumped material.

In another embodiment, the pump may be used to move fluids necessary to hydraulically operate machinery and equipment, including, but not limited to, submarines, boats, airplanes, aerospace and spacecraft. The pump may be manufactured to offer a high power to weight ratio, quiet operation, high reliability, relatively few moving parts, any and all of which may be appealing for uses with such equipment.

It is another feature that the parts for this pump are relatively simple, inexpensive, and highly reliable. The further advantage of the invention is that the pump may provide a relatively long life with few service problems.

An additional feature of this invention is that the pump may utilize single-acting or double-acting linear motors to flex the ribs. In addition, the bladder and/or ribs may utilize at least a portion of their elastic energy to assist with the pumping process.

Yet another feature of the invention is that the pump may be electrically powered to operate the linear motors to attract and/or repel the ribs. In other embodiments, the linear motors may be hydraulically operated.

It is an advantage of the present invention that friction between moving end plates and housing members may be eliminated, thereby potentially extending pump life and efficiency as compared to prior art linear pumps.

It is another advantage of the invention that inertial energy losses due to moving end plates are eliminated, thereby potentially increasing pump efficiency as compared to prior art linear pumps.

It is a further advantage of the present invention that back-pressure problems which may be encountered with prior art linear pumps due to end plates moving against the direction of fluid flow may be eliminated. The axial position of the end plates may be fixed with respect to each other during the pumping cycle.

Another advantage of the present invention that the linear pumps and/or the support ribs may be positioned external with respect to the bladder and inner chamber, or internal with respect to the bladder and inner chamber.

An additional advantage is that the linear motors may be positioned adjacent the end plates with a support rib extending between opposing linear motors, or with a linear motor positioned axially central with respect to the end plates and have a pair of support ribs each extending in an opposite direction from the linear motor to engage a respective end plate.

Yet another advantage of the invention is that the linear motors may be provided at one or both ends of a rib, or along the length of a rib.

These and further objects, features, and advantages of the present invention will become apparent from the following detailed description, wherein reference is made to the figures in the accompanying drawings.

DETAILED DESCRIPTION OF THE PREFERRED EMBODIMENTS

Figure 1:
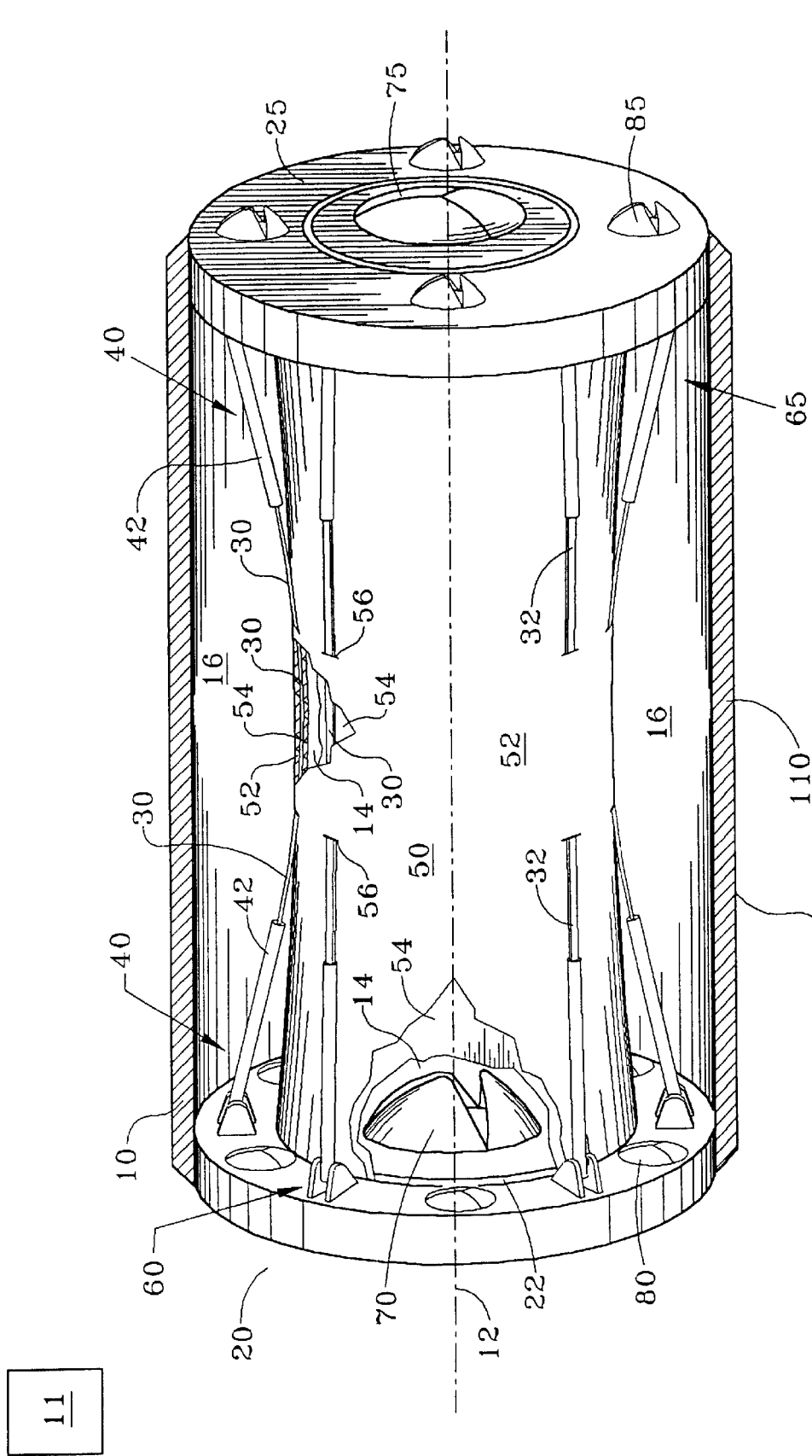
FIG. 1 illustrates a fluid pump according to the present invention in partial cross section, embodying a plurality of slat-like ribs, a semi-permeable membrane bladder and a plurality of tricuspid type check-valves, wherein the bladder and the ribs are in an expanded configuration.

FIG. 1 illustrates a preferred pump embodiment according to the present invention suitable for pumping a fluid, such as blood, water, and fluid-solid slurries. FIG. 1 illustrates a fluid pump having a pump frame 110, including a pump housing 10. The pump includes an inlet end cap/plate 20 and an outlet end cap/plate 25, each positioned on opposing ends of the housing 10 and in sealed engagement with the housing 10, forming a chamber 16 defined by the housing 10 and end caps 20, 25. The housing 10 and end caps 20, 25 may be positioned along a central axis 12.

A preferred embodiment may include the housing 10, such as illustrated in FIG. 1, forming a chamber 16 within the housing. Other pump embodiments may include a frame 110, which fixes the position of the end caps 20, 25 with respect to each other, but which does not create a chamber 16 within the frame 110 and end caps 20, 25.

A preferred embodiment of the pump also includes a flexible, conforming, generally tubular-shaped bladder 50 radially positioned about the central axis and in sealed engagement with each end cap 20,25, such as in engagement groove 22. The conforming, flexible nature of the bladder may be obtained by utilizing an elastic bladder material, although a conforming bladder may include a weave material or sections movable relative to each other to form the alternating generally cylindrical and generally hourglass configurations. An inner chamber 14 may be defined within the bladder 50 and end caps 20, 25, and the outer chamber 16 may be defined within the pump housing 10, end caps 20, 25, and external to the bladder 50. The inner chamber 14 may be hydraulically isolated from the outer chamber 16, or pump embodiments providing a selective or semi-permeable membrane bladder 50 may permit selective hydraulic connectivity between the inner 14 and outer chambers 16.

A plurality of circumferentially spaced ribs 30 may be engaged with the bladder 50, such as within bladder pockets 56. Each of the plurality of support ribs is substantially parallel to the central axis when in a resting position. In one embodiment, the bladder 50 may include an inner bladder member 54 positioned within an outer bladder member 52, and a central portion 32 the ribs 30 may be positioned between the inner 54 and outer 52 bladder members. In still other embodiments, each of the plurality of support ribs 30 and/or the plurality of linear motors 40 may be positioned radially within the bladder 50, and thus within the inner chamber 14. In such embodiment, the support ribs 30 may engage an inner surface of the bladder 50 and/or be positioned within pockets and/or attached to the inner surface of the bladder.

Each support rib 30 may be moveably engaged at opposing ends to respective opposing end caps 20, 25, such as via a hinge assembly 60 and a linear motor 40. In a preferred embodiment, each end of rib 30 may be moveably engaged with a linear motor 40, such that linear motors 40 oppose each other on each rib. Each rib 30 may also include a central portion 32 between the opposing ends of the rib 30, and more particularly between the linear motors 40. A rib 30 preferably may be engaged with a bladder 50 over at least 20 percent of the axial effective length of the rib between the end plates. An effective length of the rib may be defined as a length of a rib inclusive of any connected motors and pivot assemblies positioned between the end caps 20, 25. Thereby, an effective length may be the distance between the end caps, when the ribs 30 are in a straightened configuration. Even more preferably, a rib 30 may be engaged with a bladder over at least 50 percent of the effective length of a rib.

Figure 3:
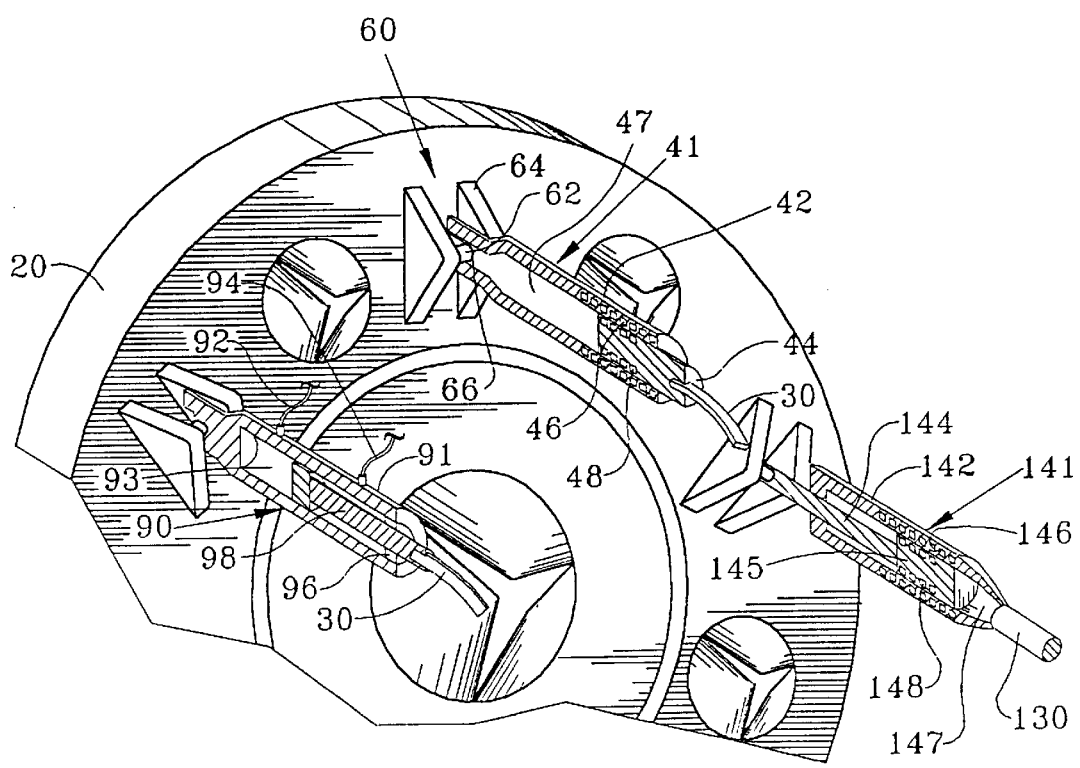
FIG. 3 illustrates a simplified cross sectional view of two electrical linear motor embodiments and one hydraulic linear motor embodiment, and further illustrating a substantially slat-shaped rib and a tubular shaped rib.

Each linear motor 40 may be pivotally engaged on one end to an end plate 20 or 25, and on an opposing end moveably engaged with a respective support rib 30. A hinge assembly 60 may be provided for pivoting the motor 40 with respect to the end plate 20 or 25. As illustrated in FIG. 3, the hinge assembly 60 may include a hinge base 64 supporting a hinge pin 62 that pivotally engages a hinge port or recess 66 on a portion of the linear motor 40. Thereby, motor pivoting may be restricted generally to within a plane extending radially from the central axis 12 and through the motor 40 and rib 30.

Figure 2:
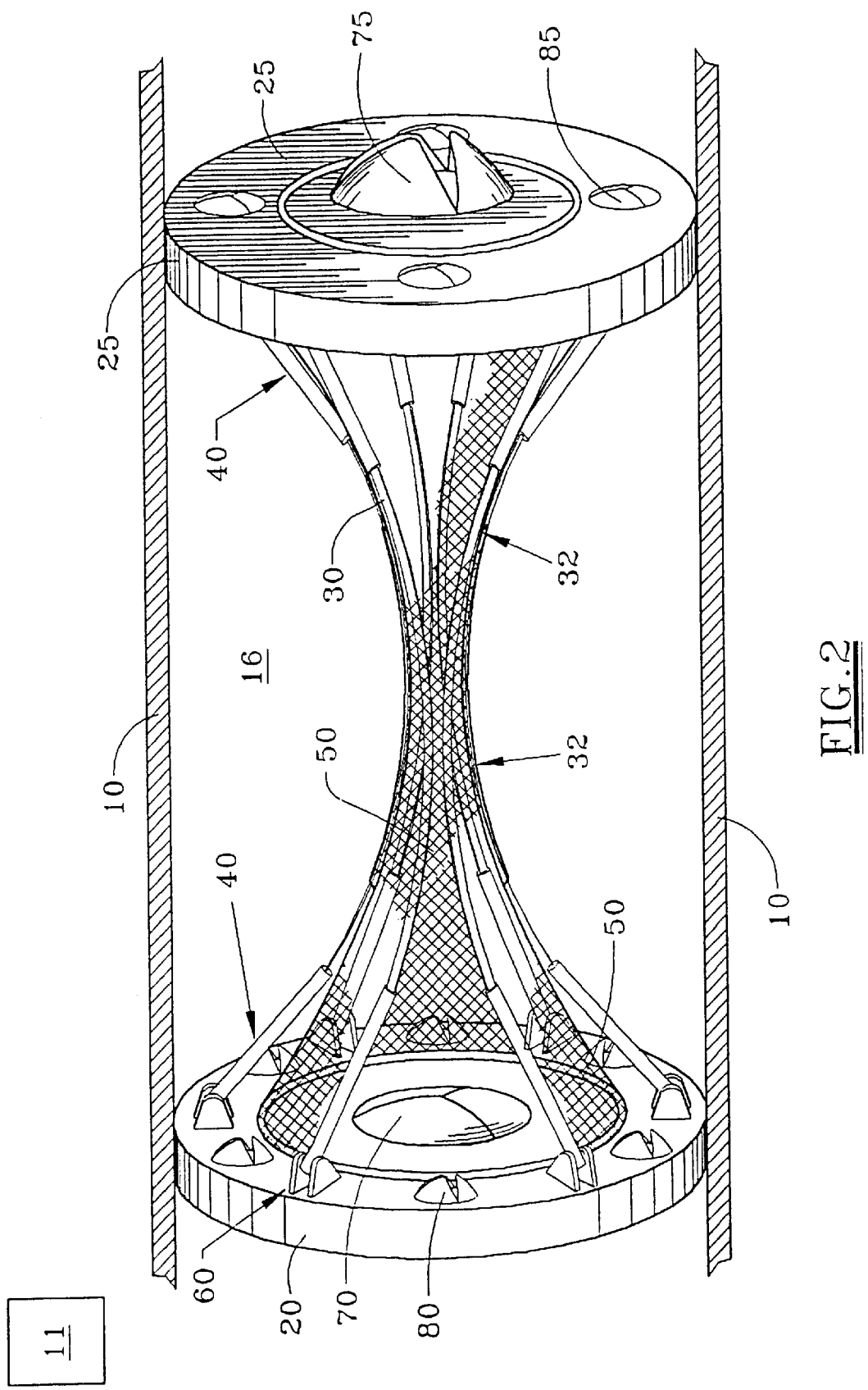
FIG. 2 illustrates the fluid pump of FIG. 1, partially in cross-section, in a condensed bladder configuration, such as after discharging fluid from the inner chamber of the bladder.

The fluid pump according to this invention may include an inner chamber inlet check valve 70, which preferably may be positioned within the inlet end cap 20, as illustrated in FIG. 1. An inner chamber outlet check valve 75 may be included, positioned within the outlet end cap 25. Pump embodiments including a housing 10 forming an outer chamber 16 may also include one or more outer chamber inner check valves 80, and one or more outer chamber outer check valves 85. The inlet 70, 80 and outlet 75, 85 check valves cooperate to facilitate selective directional fluid flow through either or both of the fluid pump chambers 14, 16. FIGS. 1, 2, and 3 illustrate use of tricuspid type check valves. Other technology advanced check valves may be used with this pump, to include but not limited to a flapper, bicuspid, ball-and-seat, and disk-and-seat type check valves. The check valves may be positioned within orifices or through bores in the end caps, such as illustrated in FIGS. 1, 2, and 3, or the check valves may be positioned upstream or downstream of the respective end caps.

The bladder 50 may be formed with a selected resting position shape such that elastic deformation of the bladder 50 stores potential energy within the bladder that is expended during the cyclical pumping operation. Such stored energy may facilitate use of single-acting linear motors, or may assist double-acting linear motors. Such selected shape may preferably be generally hour-glass or double-taper shape, such as illustrated in FIGS. 1 and 2. An hour-glass shape may be defined broadly as encompassing any shape having a smaller circumference near the axial center of the bladder, as compared to the circumference of the bladder nearer the axial ends of the bladder 50. The resting position shape may thereby exert a radially inward bias when an axially central portion of the bladder is expanded radially outward.

FIG. 2 illustrates the fluid pump illustrated in FIG. 1, wherein the plurality of linear motors 40 have been actuated to cause the plurality of support ribs to bow radially inward toward the central axis, and in the process dispelling most of the fluid from within the inner chamber 14. Each of the plurality of ribs 30 may be formed to flex in a selected orientation and positioned on the pump relative to the engaged linear motor 40 and bladder 50 such that when caused to buckle, flex, or bow, the central portion 32 of the rib bows or flexes inward toward the central axis. A circumferential width of each support rib is preferably significantly less than a radial thickness of the support rib, such that circumferential deflection is minimized during radial movement of the rib. A circumferential width of each support rib 30 may be at least two times a radial thickness of the support rib 30 and preferably at least three times a radial thickness of the support rib 30.

Rib cross-sectional thickness, shape, material and/or structural properties, may be varied along the axial length of the rib to facilitate desired flexing properties along the axial rib 30. Flexing properties may also be proscribed by geometrically varying the cross-sectional shape of the rib 30 along the axial length of the rib. For example, cross-sectional shapes of ribs or portions of ribs may be round, tubular, rectangular, T-shaped, U-shaped, triangled, oval, or flat/slat-like.

To elastically expand the bladder 50 from the constricted state, such as illustrated in FIG. 2, the ribs 30 preferably are connected to the bladder 50, such as in pockets 56 provided on an exterior surface of the bladder. A central portion of each rib may be secured to an exterior or interior surface of the bladder, between bladder layers, or through fasteners, such as loop-type fasteners.

The pump embodiment illustrated in FIG. 2 also includes a selective or semi-permeable membranous bladder 50. A fluid-solid slurry may be input into the inner chamber 14 and during pumping at least a portion of the moisture or fluid-phase may be extracted from the slurry through the bladder membrane and into the outer chamber 16. The remaining fluid-solid slurry may be pumped from the inner chamber 14 through the inner chamber outlet check valve. Thereafter, the extracted fluid may be pumped from the outer chamber 16, through the outer chamber discharge ports 85.

FIG. 2 also illustrates an embodiment of a fluid pump positioned within a housing 10 extending axially beyond the end cap 25 with respect to the central portion of the ribs 32. Such embodiment may be illustrative of a fluid pump positioned within a conduit, such as a pipeline.

FIG. 3 illustrates an embodiment of a fluid pump with the bladder 50 removed for simplicity and illustrating three embodiments of linear motors 40 for moving the ribs 30. One preferred embodiment is illustrated by linear motor assembly 41, having a motor housing or stator 42 pivotally engaged with a hinge assembly 60. The stator 42 includes an axially progressive plurality of electrical coils 46 arranged within the stator 42, and circumferentially about a housing through bore or elongated slot 47. Such coil 46 arrangement may represent an electrical powered motor, which may be controlled by a computer, responsive power source 11.

One end of a rib 30 is engaged with a shaft 44, which extends into the elongate slot 47. The shaft 44 includes a set of electrical shaft coils 48 arranged axially along a length of the shaft 44. The shaft may be defined broadly to include an end of a rib 30, as those skilled in the art will recognize that the coils 48 may be positioned on a portion of the rib 30. The shaft 44 alternatively may be connected in a conventional manner to an end of a rib 30. In still other embodiments, the shaft 44 may not include shaft coils 44, but may be a conductive rod that is moveably responsive to current in the housing coils 46. Conversely, the housing 42 may not include housing coils 46 and may be a conductive material, while the shaft 44 includes one or more shaft coils 48, whereby the shaft may move with respect to the stator 42 in response to current in the shaft coils 48.

In a preferred embodiment, each of the shaft 44 and housing 42 may include a set of electrical coils 48 and 46 respectively, such as illustrated in FIG. 3. The coils 46 and/or 48 preferably may be energized or actuated axially consecutively to effect controlled movement of the related shaft 44 and rib 30 with respect to the housing 42. Thereby, the magnitude and/or rate of flexion of the ribs may be selectively controlled to accommodate a variety of pumping conditions.

FIG. 3 also illustrates another electrical linear motor embodiment 141, having a shaft 144 pivotally connected on one end to a hinge assembly 60, and the shaft 144 including cylinder portion 145 supporting a set of electrical shaft coils 148. A portion of the shaft 144 and the coils 148 are moveably disposed within a motor stator or housing 142 supporting a set of electrical stator coils 146. FIG. 3 illustrates a substantially rod shaped support rib 130 secured to the housing 142. The stator coils 146 may be selectively energized to effect movement of the stator 142 within housing through bore 147, relative to the shaft 144, which is engaged with the end plate 20. Thereby, the magnitude and/or rate of support rib 130 flex may be selectively controlled.

FIG. 3 further illustrates a double-acting hydraulic linear motor embodiment including a hydraulic cylinder housing 91 having a housing through bore 93 and including shaft 98 moveably disposed within the through bore 93. Hydraulic fluid, which may be oil or another selected liquid or air or another selected gas, may be conducted into and from within the cylinder through bore 93 through hydraulic fluid ports 92 and 94. Rib 30, engaged with shaft 98, thereby may be controllably flexed in response to the hydraulic fluid pumped into the through bore 93.

Each of the three linear motor embodiments illustrated in FIG. 3 may be made double acting, whereby force may be exerted on the rib 30 or 130, in either axial direction by the linear motor, such that the rib may be caused to flex or to straighten out. Alternatively, each linear motor embodiment may be created as a single acting motor, such that work may be performed by the motor in one axial direction. In such single acting embodiment, potential elastic energy stored within the flexible bladder 50 and/or within the ribs 30 may perform the reciprocating work to move the plurality of support ribs 30 and bladder 50. In addition, the reciprocating work may also be performed by the fluid entering one of the chambers 14 or 16, such as into the inner chamber 14. In addition, a preferred embodiment of the fluid pump according to this invention may include a linear motor secured to each end plate 20 and 25, opposing each other and including a support rib 30 extending between and connecting the two opposing linear motors. Other embodiments may include a single linear motor secured to one of the end plates and to a support rib 30 that is engaged on an opposing end to the other end plate. Still other embodiments may include a linear motor positioned between the end plates and engaged to opposing support ribs each extending from the motor to a respective end plate. The motors may be provided external of the bladder, as depicted, but also may be provided internal of the bladder. In still other embodiments, the length of each rib, and the motors if desired, could be provided between bladder layers. The radial spacing between the bladder and the ends of the ribs and thus the motors need not be as great as shown in the figures, and is exaggerated for clarity.

Unlike many positive displacement pumps having a fixed displacement volume in a reciprocation cycle, a fluid pump according to this invention may provide a variable displacement volume per reciprocation cycle. In addition, the rate of surge or fluid acceleration during a discharge stroke may be selectively varied during the discharge stroke. Such option may be desirable in simulating the pumping characteristics of the human heart.

A power supply 11 is included to power each of the plurality of linear motors. The power may also include a control assembly and/or a programmable logic controller, such as a computer, to regulate operation of the fluid pump. The power supply may provide controlled current and/or voltage, and/or hydraulic fluid pressure and rate for hydraulically powered embodiments, to controllably operate the pump.

In some embodiments, the bladder may be at least partially self-expanding, either through elastic reflex or through another expansion mechanism, such as a second set of ribs or elastic material secured within or engaged with the bladder for expansion purposes, while the primary set of ribs 30 provide constriction or condensation of the bladder. In some embodiments, the bladder may include a plurality of axial grooves or channels within an exterior surface of the bladder, in which the ribs may moveably engage the bladder.

Figure 4:
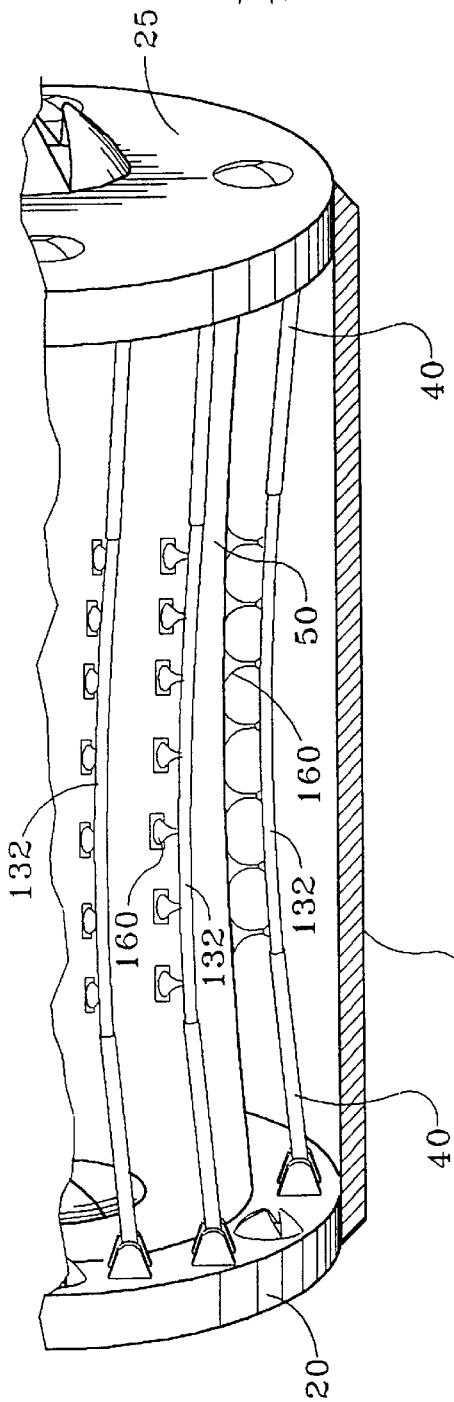
FIG. 4 illustrates an alternate embodiment of a fluid pump according to this invention, with a plurality of bladder extensions each engaged with the bladder and slidable relative to a corresponding rib.

FIG. 4 discloses an alternate embodiment of a fluid pump according to the present invention, with end plates 20 and 25 as previously described within housing 10, and a bladder extending between and sealed with the end plates. Linear motors 40 as previously described may be pivotally connected to one or both of the end plates. The linear motor, which may be a linear induction motor, may alternatively be spaced between the ends of a rib connected to the opposing end plates. FIG. 4 illustrates a plurality of bladder connectors 160 each interconnecting the bladder 52 and a revised rib 132, which is shown in greater detail in FIG. 5. As shown in FIG. 4, a plurality of bladder connectors 160 extend in rows along the length of each of the circumferentially spaced ribs, thereby structurally interconnecting the bladder 52 and a respective rib.

Figure 5:
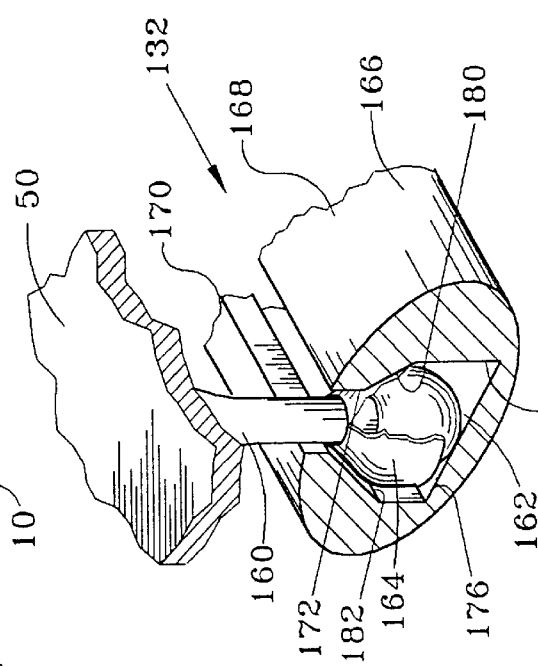
FIG. 5 illustrates a bladder extension with an enlarged lower end positioned within a slot in a rib.

FIG. 5 shows in greater detail a suitable bladder connector 160 with an enlarged end 164 radially opposite the bladder and, as shown in FIG. 5, at the lower end of the bladder connectors 160. For the FIG. 5 embodiment, an enlarged ball or other stop member 162 is provided at the lower end of the connectors 160. A cap 164, which may have a slit or cut to allow positioning over the connector 160, may be fitted above the ball. The material for the cap 164 may be plastic or may be coated to reduce frictional forces when the stop member 162 engages the side walls of the slot formed in the rib 132. In a suitable application, the rib 132 includes a neck defined by the spacing between surfaces 170 and 172 as shown in FIG. 5, and an enlarged portion defined by the spacing between surfaces 176 and 174. If desired, the diameter of the connector 160 within the neck portion of a rib may be from 80 percent to 98 percent of the width of the neck portion, while the diameter of the cap 164 is sufficient to prevent the bladder from pulling the cap through the neck portion of the slot. Accordingly, the tapered surfaces of the cap 164 conventionally engage the tapered walls 180 and 182 during flexing of the ribs and thus the bladder. This design has significant advantages since each of the bladder connectors and thus the bladder may move with respect to a rib during flexing of the rib, thereby minimizing the stress forces exerted on the bladder. In an alternate design, a plurality of stop members each at the end of a connector may be fixed to a rib, so the stop members slide within a long channel formed in the bladder. Other designs for slottably interconnecting a plurality of bladder extensions with a rib will be apparent from the embodiment shown in FIGS. 4 and 5.

Alternative embodiments may also include more support ribs than motors. A plurality of non-powered support ribs each may be engaged on opposing ends with a respective end plate. For example a pump embodiment may include a plurality of support ribs positioned circumferentially about the bladder with every other rib including a motor and the alternating ribs not including a motor. Such non-powered support ribs may provide additional bladder support.

In alternative embodiments of the fluid pump, the frame 10 and/or housing 110 may be secured to a vessel so as to move or propel the pump and vessel through a fluid body, such as a body of water. Such configuration may have particular utility in powering submarines, boats or ships. A pump or plurality of pumps according to this invention engaged with a vessel may provide relatively quiet propulsion.

It may be appreciated that various changes to the details of the illustrated embodiments and systems disclosed herein, may be made without departing from the spirit of the invention. While preferred and alternative embodiments of the present invention have been described and illustrated in detail, it is apparent that still further modifications and adaptations of the preferred and alternative embodiments will occur to those skilled in the art. However, it is to be expressly understood that such modifications and adaptations are within the spirit and scope of the present invention, which is set forth in the following claims.

What is claimed is:

1. A fluid pump for pumping a fluid, comprising:
   a pump frame having a central axis extending axially between an inlet end and an outlet end;
   an inlet end cap and an outlet end cap each secured to the pump frame and spaced axially from each other;
   a plurality of circumferentially spaced support ribs each extending between the inlet end cap and the outlet end cap, each support rib having a central portion between the end caps radially moveable with respect to the central axis;
   a plurality of linear motors each connected to a respective support rib, each linear motor including a stator and a shaft linearly moveable relative to the stator to cyclically increase and decrease an effective length of the rib to radially move the central portion of the rib;
   a conforming generally tubular bladder radially positioned by the plurality of support ribs and interconnected at one end to said inlet end cap and at an opposite end to said outlet end cap, the bladder defining an inner chamber therein and between the end caps, the inner chamber having a volume;
   an inner chamber inlet check valve fluidly interconnecting the fluid with the inner chamber;
   an inner chamber outlet check valve fluidly interconnecting the inner chamber with the fluid; and
   a power supply for powering each of the plurality of linear motors to cyclically move the plurality of support ribs and thereby vary the volume of the inner chamber to pump fluid.

2. A fluid pump as defined in claim 1, further comprising:
   the frame including a housing having a throughbore and a housing axis along the central axis;
   an outer chamber between the bladder, the housing, and the end caps;
   at least one outer chamber inlet check valve fluidly interconnecting the fluid with the outer chamber; and
   at least one outer chamber outlet check valve fluidly interconnecting the outer chamber with the fluid.

3. A fluid pump as defined in claim 1, wherein the linear motor associated with each rib further comprises:
   an inlet stator pivotally attached to the inlet end cap;
   an outlet stator pivotally attached to the outlet end cap; and
   the support rib extending between the inlet stator and the outlet stator; and
   the power supply simultaneously extends and retracts the support rib relative to both the inlet stator and the outlet stator.

4. The fluid pump as defined in claim 1, wherein the linear motor associated with each rib further comprises:
   the stator pivotally attached to one of the inlet end cap and the outlet end cap; and
   the support rib secured at one end to the other of the inlet end cap and the outlet end cap, and an opposing end of the rib moveably engaged with the respective stator.

5. The fluid pump as defined in claim 1, wherein the linear motor associated with each rib further comprises:
   the stator secured to an end of the a respective support rib and the shaft pivotally attached to one of the inlet end cap and the outlet end cap.

6. The fluid pump as defined in claim 1, wherein a circumferential width of each support rib is significantly greater than a radial thickness of the support rib, such that circumferential deflection is minimized during radial movement of the rib.

7. The fluid pump as defined in claim 1, wherein the linear motor is electrically powered by the power supply.

8. The fluid pump as defined in claim 1, wherein the linear motor is hydraulically powered by the power supply, such that the stator is a hydraulic cylinder and the shaft is a rod axially moveable relative to the hydraulic cylinder.

9. The fluid pump as defined in claim 1, wherein the flexible generally tubular bladder is formed with a generally hour-glass shape when in a resting position, such that the bladder exerts a radially inward bias when an axially central portion is expanded radially outward, and each of the plurality of support ribs is formed as a relatively axially straight member when in a resting position, such that each of the plurality of support ribs exerts a radially outward bias that opposes the radially inward bias of the bladder when the respective support rib is moved radially inward.

10. The fluid pump as defined in claim 1, wherein each of the plurality of linear motors is positioned external of the bladder.

11. The fluid pump as defined in claim 1, wherein the flexible generally tubular bladder is secured to each rib along at least 20 percent of the axial effective length of the rib between the end plates.

12. The fluid pump as defined in claim 1, further comprising:
    a plurality of connectors each extending radially from one of the bladder and a support rib and having an enlarged end; and
    the other of the bladder and the support rib including an elongated slot for receiving the enlarged end of each of the plurality of connectors, such that the connectors may move along the elongated slot.

13. A method of pumping a fluid using a fluid pump, the method comprising:
    providing a pump frame having a central axis extending axially between an inlet end and an outlet end;
    securing each of an inlet end cap and an outlet end cap to the pump frame and spaced axially from each other;
    extending each of a plurality of circumferentially spaced support ribs between the inlet end cap and the outlet end cap, each support rib having a central portion between the end caps radially moveable with respect to the central axis;
    connecting each of a plurality of linear motors with a respective support rib, each linear motor including a stator and a shaft linearly moveable relative to the stator;
    interconnecting a flexible generally tubular bladder to said inlet end cap and interconnecting an opposite end of the bladder to said outlet end cap, the bladder defining an inner chamber therein and between the end caps, the inner chamber having a volume;
    interconnecting a central portion of the bladder between the end caps with the central portion of each of the plurality of support ribs;
    fluidly interconnecting the fluid with the inner chamber using an inner chamber inlet check valve;

fluidly interconnecting the inner chamber with the fluid using an inner chamber outlet check valve; and powering each of the plurality of linear motors with a power supply to cyclically increase and decrease an effective length of each of the plurality of support ribs to radially move the central portion of the ribs and thereby vary a volume of the inner chamber.

14. The method of pumping fluid as defined in claim 13, further comprising:

providing the frame with a housing having a throughbore and a housing axis along the central axis;

engaging the housing with each of the inlet end cap outlet end cap to define an outer chamber between the bladder, the housing, and the end caps;

fluidly interconnecting the fluid with the outer chamber using at least one outer chamber inlet check valve;

fluidly interconnecting the outer chamber with the fluid using at least one outer chamber outlet check valve; and powering each of the plurality of linear motors includes varying a volume of the outer chamber to pump fluid through the outer chamber.

15. The method of pumping fluid as defined in claim 13, wherein engaging each of a plurality of linear motors with a respective rib further comprises:

pivotally attaching an inlet stator to the inlet end cap;

pivotally attaching an outlet stator to the outlet end cap; and extending the support rib between the inlet stator and the outlet stator; and simultaneously extending and retracting the support rib relative to both the inlet stator and the outlet stator using a power supply.

16. The method of pumping fluid as defined in claim 13, wherein engaging each of a plurality of linear motors with a respective rib further comprises:

pivotally attaching the stator to one of the inlet end cap and the outlet end cap; and securing one end of the support rib to the other of the inlet end cap and the outlet end cap; and moveably engaging an opposing end of the rib with the respective stator.

17. The method of pumping fluid as defined in claim 13, further comprising:

forming each support rib wherein a circumferential width of each support rib is significantly less than a radial thickness of the respective support rib, such that circumferential deflection is minimized during radial movement of the rib.

18. The method of pumping fluid as defined in claim 13, further comprising:

forming the flexible generally tubular bladder with a generally hour-glass shape when in a resting position, such that the bladder exerts a radially inward bias when an axially central portion is expanded radially outward.

19. The method of pumping fluid as defined in claim 18, further comprising:

forming each of the plurality of support ribs as a relatively straight member when in a resting position, such that each of the plurality of support ribs exerts an outward bias that opposes the inward bias of the bladder when the respective support rib is moved radially inward.

20. The method of pumping fluid as defined in claim 18, further comprising:

securing the pump frame to a vessel to propel the vessel through a fluid.

21. The method of pumping fluid as defined in claim 13, further comprising:

positioning each of the plurality of linear motors radially outward of the bladder.

22. The method of pumping fluid as described in claim 13, further comprising:

connecting a plurality of connectors to one of the bladder and the support rib, each connector having an enlarged end, and providing an elongate slot in the other of the bladder and the support rib for receiving the enlarged end of each of the plurality of connectors, such that the connectors may move along the elongate slot.

* * * * *